(12) United States Patent
Tanimoto et al.

(10) Patent No.: US 11,234,439 B2
(45) Date of Patent: Feb. 1, 2022

(54) IMIDE COMPOUND AND USE THEREOF

(71) Applicant: SUMITOMO CHEMICAL COMPANY, LIMITED, Tokyo (JP)

(72) Inventors: Masaya Tanimoto, Anpachi-gun (JP); Koichiro Dota, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 419 days.

(21) Appl. No.: 16/330,430

(22) PCT Filed: Aug. 29, 2017

(86) PCT No.: PCT/JP2017/030861
§ 371 (c)(1),
(2) Date: Mar. 5, 2019

(87) PCT Pub. No.: WO2018/047670
PCT Pub. Date: Mar. 15, 2018

(65) Prior Publication Data
US 2021/0274786 A1 Sep. 9, 2021

(30) Foreign Application Priority Data

Sep. 7, 2016 (JP) .............................. JP2016-174381
Nov. 28, 2016 (JP) .............................. JP2016-229797

(51) Int. Cl.
*C07D 231/14* (2006.01)
*A01N 43/56* (2006.01)

(52) U.S. Cl.
CPC ........... *A01N 43/56* (2013.01); *C07D 231/14* (2013.01)

(58) Field of Classification Search
CPC .................................................. C07D 231/14
See application file for complete search history.

(56) References Cited

U.S. PATENT DOCUMENTS

| | | | |
|---|---|---|---|
| 5,093,347 A | 3/1992 | Graneto et al. | |
| 8,580,836 B2 | 11/2013 | Matsuzaki et al. | |
| 9,192,160 B2 | 11/2015 | Venturini et al. | |
| 2004/0138265 A1 | 7/2004 | Walter et al. | |
| 2007/0197556 A1 | 8/2007 | Tormo I Blasco et al. | |
| 2009/0105325 A1 | 4/2009 | Furuya et al. | |

FOREIGN PATENT DOCUMENTS

| | | |
|---|---|---|
| EP | 0569505 B1 | 12/1994 |
| EP | 2584902 B1 | 7/2015 |
| JP | 6-505252 A | 6/1994 |
| JP | 2004-519464 A | 7/2004 |
| JP | 2007-537192 A | 12/2007 |
| JP | 2011-231062 A | 11/2011 |
| WO | WO 92/12970 A1 | 8/1992 |
| WO | WO 97/47589 A1 | 12/1997 |
| WO | WO 02/059086 A1 | 8/2002 |
| WO | WO 2005/110089 A2 | 11/2005 |
| WO | WO 2007/020986 A1 | 2/2007 |
| WO | WO 2011/135836 A1 | 11/2011 |
| WO | WO 2011/135839 A1 | 11/2011 |
| WO | WO 2011/162397 A1 | 12/2011 |
| WO | WO 2012/084812 A1 | 6/2012 |
| WO | WO 2013/167545 A1 | 11/2013 |
| WO | WO 2013/167549 A1 | 11/2013 |

OTHER PUBLICATIONS

Colombian Office Action and Search Report for Colombian Application No. NC2019/002394, dated Jan. 22, 2020, with an English translation.
Chilean Office Action and Search Report (including an English translation thereof) issued in the corresponding Chilean Patent Application No. 201900572 dated Sep. 24, 2020.
Indonesian Office Action (including an English translation thereof) issued in the corresponding Indonesian Patent Application No. PID201902138 dated Feb. 22, 2021.
English translation of the International Preliminary Report on Patentability and Written Opinion of the International Searching Authority for International Application No. PCT/JP2017/030861, dated Mar. 12, 2019.
English translation of the International Search Report for International Application No. PCT/JP2017/030861, dated Nov. 28, 2017.
Indian Examination Report issued in the corresponding Indian Patent Application No. 201937013418 dated Oct. 20, 2020.

*Primary Examiner* — Shawquia Jackson
(74) *Attorney, Agent, or Firm* — Birch, Stewart, Kolasch & Birch, LLP

(57) ABSTRACT

An imide compound represented by formula (I)

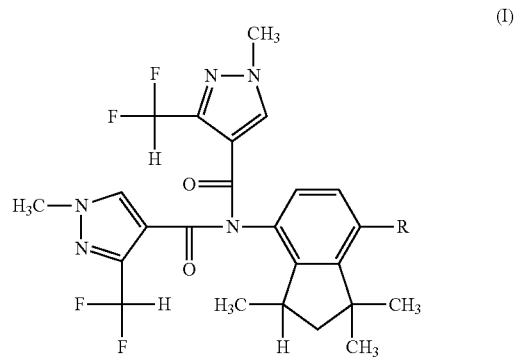

[wherein R represents a fluorine atom or a hydrogen atom] has excellent control efficacies against plant diseases.

6 Claims, No Drawings

IMIDE COMPOUND AND USE THEREOF

TECHNICAL FIELD

The present invention relates to imide compounds and use thereof.

BACKGROUND ART

Various compounds for controlling plant diseases have been developed so far (see Patent Document 1).

CITATION LIST

Patent Document

Patent Document 1: WO 02/059086 pamphlet

SUMMARY OF THE INVENTION

Problems to be Solved by Invention

An object of the present invention is to provide compounds having excellent control efficacies against plant diseases.

Means to Solve Problems

The present inventors have studied to find out compounds having excellent control efficacies against plant diseases. As a result, they have found out that an imide compound represented by the following formula (I) has excellent control efficacies against plant diseases.

Namely, the present invention provides the followings.

[1] An imide compound represented by formula (I)

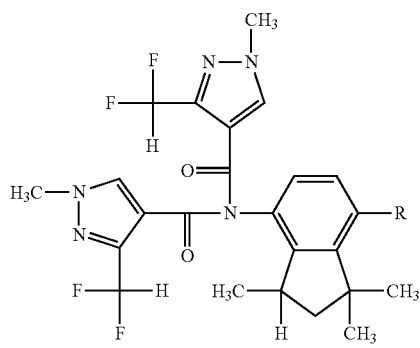

(I)

[wherein R represents a fluorine atom or a hydrogen atom] (hereinafter referred to as "Present compound").

[2] The imide compound according to [1], wherein the imide compound represented by formula (I) is an imide compound represented by formula (II)

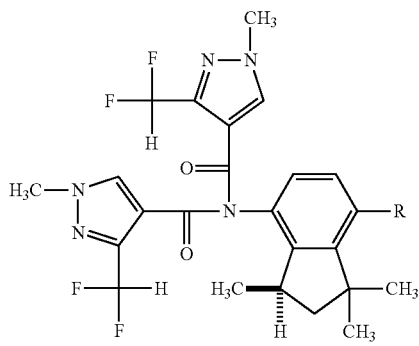

(II)

[wherein R represents a fluorine atom or a hydrogen atom] (hereinafter referred to as "Compound (II)").

[3] An agent for controlling a plant disease comprising the imide compound according to [1] or [2] and an inert carrier (hereinafter referred to as "Present control agent").

[4] A method for controlling a plant disease which comprises applying an effective amount of the imide compound according to [1] or [2] to a plant or soil.

[5] Use of the imide compound according to [1] or [2] for controlling a plant disease.

[6] A composition comprising an imide compound represented by formula (I)

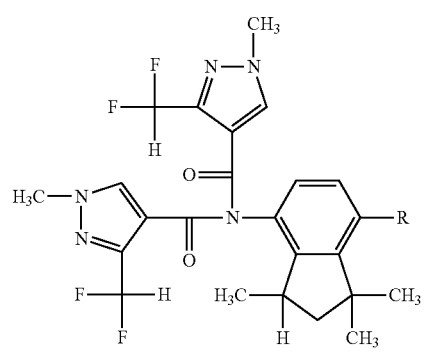

(I)

[wherein R represents a fluorine atom or a hydrogen atom] and one or more ingredient (s) selected from the group consisting of an insecticidal active ingredient, a miticidal active ingredient, a nematicidal active ingredient, a plant growth regulatory ingredient, a synergist, and another ingredient for controlling a plant disease.

The present invention can control plant diseases.

MODE FOR CARRYING OUT THE INVENTION

Examples of the Present compound include the following compounds.

The Present compound, wherein R is a fluorine atom;
The Present compound, wherein R is a hydrogen atom;
The Compound (II), wherein R is a fluorine atom;
The Compound (II), wherein R is a hydrogen atom;
A compound which comprises the Compound (II) and an imide compound represented by formula (III)

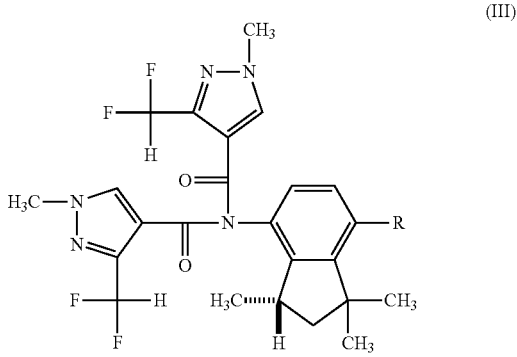

(hereinafter referred to as "Compound (III)") in a ratio of 1/1 to 100000/1;

A compound which comprises the Compound (II) wherein R is a fluorine atom and the Compound (III) wherein R is a fluorine atom in a ratio of 1/1 to 100000/1;

A compound which comprises the Compound (II) wherein R is a hydrogen atom and the Compound (III) wherein R is a fluorine atom in a ratio of 1/1 to 100000/1;

A compound which comprises the Compound (II) and the Compound (III) in a ratio of 4/1 to 100000/1;

A compound which comprises the Compound (II) wherein R is a fluorine atom and the Compound (III) wherein R is a fluorine atom in a ratio of 4/1 to 100000/1;

A compound which comprises the Compound (II) wherein R is a hydrogen atom and the Compound (III) wherein R is a hydrogen atom in a ratio of 4/1 to 100000/1;

The Present control agent comprises the Present compound and an inert carrier. The Present control agent is usually prepared by mixing the Present compound with an inert carrier such as a solid carrier and a liquid carrier, an oil, a surfactant, and/or the others, and if necessary, adding an auxiliary agent for formulation such as a binder, a dispersant, and a stabilizer, to formulate into a wettable powder, a granular wettable powder, a flowable, a granule, a dry flowable, an emulsifiable concentrate, an aqueous solution, an oil solution, a smoking agent, an aerosol, a microcapsule, or the others. Such formulations comprise usually 0.1 to 99% by weight, preferably 0.2 to 90% by weight of the Present compound.

Examples of the solid carrier include fine powders or granules of clays (for example, kaolin clay, diatomaceous earth, synthetic hydrated silicon oxides, Fubasami clay, bentonite, or acid white clay), talcs, other inorganic minerals (for example, sericite, quartz powder, sulfur powder, active carbon, or calcium carbonate), and the others.

Examples of the liquid carrier include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles; ethers (for example, diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, or 3-methoxy-3-methyl-1-butanol); amides; and sulfoxides.

Examples of the surfactant include alkyl sulfates, alkyl sulfonates, alkyl aryl sulfonates, alkyl aryl ethers and polyoxyethylated compounds thereof, polyoxyethylene glycol ethers, polyhydric alcohol esters, and sugar alcohol derivatives.

Examples of the other auxiliary agents for formulation include binders, dispersants, and stabilizers. Specific examples thereof include casein, gelatin, polysaccharides (for example, starch, gum arabic, cellulose derivatives, or alginic acid), lignin derivatives, bentonite, saccharides, water-soluble synthetic polymers (for example, polyvinyl alcohol, polyvinyl pyrrolidone, or polyacrylic acids), acidic isopropyl phosphate, 2,6-di-tert-butyl-4-methylphenol, BHA (a mixture of 2-tert-butyl-4-methoxyphenol and 3-tert-butyl-4-methoxyphenol), vegetable oils, mineral oils, and fatty acids.

Examples of the oil and the surfactant which may be mixed with and used in combination with the Present compound include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), and BANOLE (registered trademark).

The Present compound is applied in the form of the Present control agent. The method for applying the Present control agent is not limited to a specific method as long as the Present control agent can be substantially applied. Examples of the method include an application to a plant body such as a foliar application, an application to a cultivation area of plant such as a soil treatment, and an application to seeds such as a seed disinfection.

The amount of the Present compound to be applied in the method for control of the present invention varies depending on type of plant to be treated, type or frequency of occurrence of plant disease to be controlled, dosage form, time of treatment, method for treatment, place to be treated, weather conditions, and the others. When applied to foliage of a plant or soil for cultivating a plant, the amount of the Present compound is usually 1 to 500 g per 1000 m$^2$.

An emulsifiable concentrate, a wettable powder, a flowable, or the like is usually applied by diluting it with water, and then spreading it. In this case, the concentration of the Present compound is usually within the range of 0.0005 to 2% by weight. A dust, a granule, or the like is usually applied as itself without diluting it.

The Present compound may be used as an agent for controlling plant diseases in croplands such as fields, paddy fields, grasses, and orchards. The Present compound can control diseases in the croplands etc. for cultivating the following plant(s) etc.

Crops: corn, rice, wheat, barley, rye, oat, sorghum, cotton, soybean, peanut, buckwheat, beet, rapeseed, sunflower, sugar cane, tobacco, and the others;

Vegetables: solanaceous vegetables (for example, eggplant, tomato, pimento, pepper, or potato), cucurbitaceous vegetables (for example, cucumber, pumpkin, zucchini, water melon, or melon), cruciferous vegetables (for example, Japanese radish, white turnip, horseradish, kohlrabi, Chinese cabbage, cabbage, leaf mustard, broccoli, or cauliflower), asteraceous vegetables (for example, burdock, crown daisy, artichoke, or lettuce), liliaceous vegetables (for example, welsh onion, onion, garlic, or asparagus), ammiaceous vegetables (for example, carrot, parsley, celery, or parsnip), chenopodiaceous vegetables (for example, spinach or Swiss chard), lamiaceous vegetables (for example, perilla, mint, or basil), strawberry, sweet potato, glutinous yam, eddoe, and the others; Flowers;

Foliage plants;

Fruits: pomaceous fruits (for example, apple, pear, Japanese pear, Chinese quince, or quince), stone fleshy fruits (for example, peach, plum, nectarine, Japanese apricot (Prunus mume), cherry fruit, apricot, or prune), citrus fruits (for example, Citrus unshiu, orange, lemon, lime, or grapefruit), nuts (for example, chestnuts, walnuts, hazelnuts, almond, pistachio, cashew nuts, or macadamia nuts), berry fruits (for example, blueberry, cranberry, blackberry, or raspberry), grapes, Japanese persimmon, olive, Japanese plum, banana, coffee, date palm, coconuts, and the others; and Trees other than fruit trees: tea, mulberry, flowering plants, roadside trees (for example, ash, birch, dogwood, eucalyptus, ginkgo (*Ginkgo biloba*), lilac, maple, oak (quercus), poplar, Judas tree, Formosan gum (*Liquidambar formosana*), plane tree, zelkova, Japanese arborvitae (*Thuja standishii*), fir wood, hemlock, juniper, pinus, picea, or yew (*Taxus cuspidate*)), and the others.

The above-mentioned "plant(s)" may include genetically modified plant(s).

Examples of the plant disease which can be controlled by the Present compound include diseases caused by a plant pathogen such as filamentous fungi and bacteria. Specific examples of the plant disease include the followings. The scientific name of each pathogen which causes the disease is shown in parentheses.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*);

Wheat diseases: powdery mildew (*Blumeria graminis*), Fusarium blight (*Fusarium graminearum, Fusarium avenaceum, Fusarium culmorum, Microdochium nivale*), stripe rust (*Puccinia striiformis*), stem rust (*Puccinia graminis*), leaf rust (*Puccinia recondita*), snow mold (*Microdochium nivale, Microdochium majus*), typhula snow blight (*Typhula incarnata, Typhula ishikariensis*), loose smut (*Ustilago tritici*), stinking smut (*Tilletia caries, Tilletia controversa*), eyespot (*Pseudocercosporella herpotrichoides*), Septoria leaf blotch (*Septoria tritici*), glume blotch (*Stagonospora nodorum*), tan spot (*Pyrenophora tritici*-repentis), damping-off caused by *rhizoctonia* fungus (*Rhizoctonia solani*), and damping-off (*Gaeumannomyces graminis*);

Barley diseases: powdery mildew (*Blumeria graminis*), Fusarium blight (*Fusarium graminearum, Fusarium avenaceum, Fusariura culmorum, Microdochim nivale*), stripe rust (*Puccinia striiformis*), stem rust (*Puccinia graminis*), leaf rust (*Puccinia hordei*), dwarf leaf rust (*Puccinia hordei*), loose smut (*Ustilago nuda*), scald (*Rhynchosporium secalis*), net blotch (*Pyrenophora teres*), spot blotch (*Cochliobolussativus*), leaf stripe (*Pyrenophora graminea*), Ramuraria leaf spot (*Ramularia collo-*cygni), and damping-off caused by *rhizoctonia* fungus (*Rhizoctonia solani*);

Corn diseases: rust (*Puccinia sorghi*), southern rust (*Puccinia polysora*), northern leaf blight (*Setosphaeria turcica*), tropical rust (*Physopella zeae*), southern leaf blight (*Cochliobolus heterostrophus*), anthracnose (*Colletotrichum graminicola*), gray leaf spot (*Cercospora zeae-*maydis), eyespot (*Kabatiella zeae*), Phaeosphaeria leaf spot (*Phaeosphaeria maydis*), Stenocarpella maydis, *Stenocarpella macrospora*, stalk rot (*Fusarium graminearum, Fusarium verticilioides, Colletotrichum graminicola*), and smut (*Ustilago maydis*);

Cotton diseases: anthracnose (*Colletotrichum gossypii*), areolate mildew (*Ramularia areola*), leaf spot (*Alternaria macrospora, Alternaria gossypii*), and Black root rot caused by *Thielaviopsis* fungus (*Thielaviopsis basicola*);

Coffee diseases: rust (*Hemileia vastatrix*) and leaf spot (*Cercospora coffeicola*);

Rapeseed diseases: sclerotinia rot (*Sclerotinia sclerotiorum*), alternaria leaf spot (*Alternaria brassicae*), and root rot (*Phoma lingam*);

Sugarcane diseases: rust (*Puccinia melanocephela, Puccinia kuehnii*) and smut (*Ustilago scitaminea*);

Sunflower diseases: rust (*Puccinia helianthi*) and downy mildew (*Plasmopara halstedii*);

Citrus diseases: melanose (*Diaporthe citri*), scab (*Elsinoe fawcetti*), fruit rot (*Penicillium digitatum, Penicillium italicum*), and Phytophthora disease (*Phytophthora parasitica, Phytophthora citrophthora*);

Apple diseases: blossom blight (*Monilinia mali*), canker (*Valsa ceratosperma*), powdery mildew (*Podosphaera leucotricha*), Alternaria leaf spot (*Alternaria alternata* apple pathotype), scab (*Venturia inaequalis*), anthracnose (*Glomerella cingulata*), blotch (*Diplocarpon mali*), ring rot (*Botryosphaeria berengeriana*), and crown rot (*Phytophtora cactorum*);

Pear diseases: scab (*Venturia nashicola, Venturia pirina*), black spot (*Alternaria alternata* Japanese pear pathotype), and rust (*Gymnosporangium haraeanum*);

Peach diseases: brown rot (*Monilinia fructicola*), scab (*Cladosporium carpophilum*), and Phomopsis rot (*Phomopsis sp.*);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*);

Diseases of Japanese persimmon: anthracnose (*Gloeosporium kaki*) and leaf spot (*Cercospora kaki, Mycosphaerella nawae*);

Diseases of Cucurbitaceae: anthracnose (*Colletotrichum lagenarium*), powdery mildew (*Sphaerotheca fuliginea*), gummy stem blight (*Didymella bryoniae*), corynespora leaf spot (*Corynespora cassiicola*), Fusarium wilt (*Fusarium oxysporum*), downy mildew (*Pseudoperonospora cubensis*), Phytophthora rot v (*Phytophthora* sp.), and damping-off (*Pythium* sp.);

Tomato diseases: early blight (*Alternaria solani*), leaf mold (*Cladosporium fulvum*), cercospora leaf mold (*Pseudocercospora fuligena*), late blight (*Phytophthora infestans*), and powdery mildew (*Leveillula taurica*);

Eggplant diseases: brown spot (*Phomopsis vexans*) and powdery mildew (*Erysiphe cichoracearum*);

Diseases of brassica family: Alternaria leaf spot (*Alternaria japonica*), white spot (*Cercosporella brassicae*), clubroot (*Plasmodiophora brassicae*), and downy mildew (*Peronospora parasitica*);

Welsh onion diseases: rust (*Puccinia allii*);

Soybean diseases: purple stain (*Cercospora kikuchii*), Sphaceloma scad (*Elsinoe glycines*), pod and stem blight (*Diaporthe phaseolorum* var. sojae), rust (*Phakopsora pachyrhizi*), target spot (*Corynespora cassiicola*), anthracnose (*Colletotrichum glycines, Colletotrichum truncatum*), Rhizoctonia rot (*Rhizoctonia solani*), septoria brown spot (*Septoria glycines*), Cercospora leaf spot (*Cercospora sojina*), sclerotinia rot (*Sclerotinia sclerotiorum*), powdery mildew (*Microsphaera diffusa*), phytophthora root and stem rot (*Phytophthora sojae*), downy mildew (*Peronospora manshurica*), and sudden death syndrome (*Fusarium virguliforme*);

Kidney bean diseases: stem rot (*Sclerotinia sclerotiorum*), rust (*Uromyces appendiculatus*), angular leaf spot (*Phaeoisariopsis griseola*), and anthracnose (*Colletotrichum lindemuthianum*);

Peanut diseases: leaf spot (*Cercospora personata*), brown leaf spot (*Cercospora arachidicola*), and southern blight (*Sclerotium rolfsii*);

Garden pea diseases: powdery mildew (*Erysiphe pisi*);

Potato diseases: early blight (*Alternaria solani*), late blight (*Phytophthora infestans*), pink rot (*Phytophthora erythroseptica*), powdery scab (*Spongospora subterranea* f. sp. *subterranea*), and Verticillium wilt (*Verticillium alboatrum, Verticillium dahliae, Verticillium nigrescens*);

Strawberry diseases: powdery mildew (*Sphaerotheca humuli*);

Tea diseases: net blister blight (*Exobasidium reticulatum*), white scab (*Elsinoe leucospila*), gray blight (*Pestalotiopsis* sp.), and anthracnose (*Colletotrichum theae*-sinensis);

Tabacco diseases: brown spot (*Alternaria longipes*), anthracnose (*Colletotrichum tabacum*), downy mildew (*Peronospora tabacina*), and black shank (*Phytophthora nicotianae*);

Sugar beet diseases: cercospora leaf spot (*Cercospora beticola*), leaf blight (*Thanatephorus cucumeris*), root rot (*Thanatephorus cucumeris*), aphanomyces root rot (*Aphanomyces cochlioides*), and rust (*Uromyces betae*);

Rose diseases: black spot (*Diplocarpon rosae*) and powdery mildew (*Sphaerotheca pannosa*);

*Chrysanthemum* and Asteraceae vegetable diseases: leaf blight (*Septoriachrysanthemi*-indici) and white rust (*Puccinia horiana*);

Onion diseases: Botrytis leaf blight (*Botrytis cinerea, Botrytis byssoidea, Botrytis squamosa*), neck rot (*Botrytis allii*), and small sclerotial (*Botrytis squamosa*);

Various plants diseases: gray mold (*Botrytis cinerea*) and Sclerotinia rot (*Sclerotinia sclerotiorum*);

Japanese radish diseases: Alternaria leaf spot (*Alternaria brassicicola*);

Turfgrass diseases: dollar spot (*Sclerotiniahomoeocarpa*) and brown patch and large patch (*Rhizoctonia solani*);

Banana diseases: Sigatoka disease (*Mycosphaerella fijiensis, Mycosphaerella musicola*);

Seed diseases or diseases in the early stages of the growth of various plants caused by bacteria of *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp., *Diplodia* spp., or the others;

Viral diseases of various plants mediated by *Polymyxa* spp., *Olpidium* spp., or the others;

rice bacterial seedling blight (*Burkholderia plantarii*); cucumber angular leaf spot (*Pseudomonas syringae* pv. *Lachrymans*);

eggplant bacterial wilt (*Ralstonia solanacearum*); citrus canker (*Xanthomonas citri*);

Chinese cabbage bacterial soft rot (*Erwinia carotovora*); and the others.

EXAMPLES

The following Examples including Preparation Examples, Formulation Examples, and Test Examples serve to illustrate the present invention more in detail, which should not intend to limit the present invention.

First, regarding the preparation of the Present compound, the Preparation Examples are shown below.

Preparation Example 1

(R)-1,1,3-trimethyl-4-aminoindane (0.20 g) (optical purity 96%), diisopropylethylamine (1.2 mL), 4-dimethylaminopyridine (0.02 g), tetraethylene glycol dimethyl ether (5 mL), and 1-methyl-3-difluoromethylpyrazole-4-carboxylic acid chloride (0.46 g) were mixed, and the resulting mixture was stirred at 80° C. for 1 hour, and then stirred at 120° C. for 5 hours. The reaction mixture was cooled to room temperature, and then water, toluene, and 5% hydrochloric acid were added thereto to separate the resulting mixture. The resulting organic layer was sequentially washed with water, saturated sodium bicarbonate water, and water, then dried over magnesium sulfate, and concentrated under reduced pressure. The resulting residues were subjected to silica gel column chromatography to give the following compound (hereinafter referred to as Present Compound "(1)") (optical purity 99.9%).

Present Compound (1)

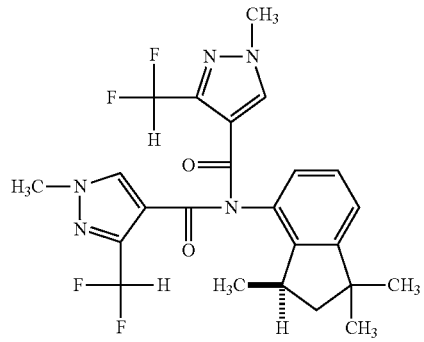

$^1$H-NMR (CDCl$_3$) δ: 7.51 (1H, s), 7.32 (1H, dd, J=7.2 Hz, 7.8 Hz), 7.22 (1H, d, J=7.2 Hz), 7.13 (1H, t, J=54 Hz), 7.07 (1H, d, J=7.8 Hz), 6.96 (1H, t, J=54 Hz), 6.52 (1H, s), 3.89 (3H, s), 3.72 (3H, s), 2.91-2.83 (1H, m), 2.05 (1H, dd, J=4.8 Hz, 7.8 Hz), 1.57 (1H, dd, J=7.8 Hz, 12.6 Hz), 1.36 (3H, s), 1.24 (3H, d, J=13.8 Hz), 0.98 (3H, s). [α]$_D^{22}$=+113.5° (CHCl$_3$, c1.1)

Preparation Example 2

The following Present Compound (2) was prepared by using 7-fluoro-1,1,3-trimethyl-4-aminoindane instead of (R)-1,1,3-trimethyl-4-aminoindane according to the method described in the Preparation Example 1.

Present Compound (2)

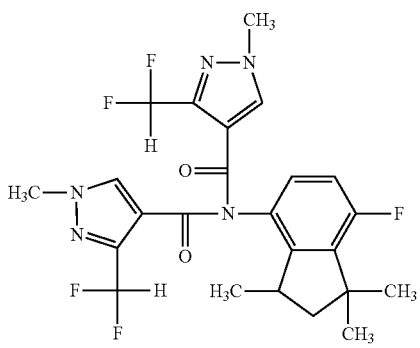

¹H-NMR (CDCl₃) δ: 7.53 (1H, s), 7.10 (1H, t, J=53.8 Hz), 7.06 (1H, dd, J=8.8, 4.4 Hz), 6.98 (1H, t, J=8.8 Hz), 6.93 (1H, t, J=54.5 Hz), 6.71 (1H, s), 3.91 (3H, s), 3.78 (3H, s), 2.97-2.88 (1H, m), 2.07 (1H, dd, J=12.9, 8.1 Hz), 1.62 (1H, dd, J=12.9, 8.1 Hz), 1.58 (3H, s), 1.48 (3H, s), 1.24 (3H, d, J=6.9 Hz).

Preparation Example 3

The following Present Compound (3) was prepared by using 1,1,3-trimethyl-4-aminoindane instead of (R)-1,1,3-trimethyl-4-aminoindane according to the method described in the Preparation Example 1.

Present Compound (3)

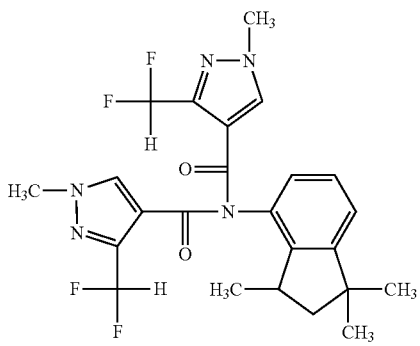

¹H-NMR (CDCl₃) δ: 7.51 (1H, s), 7.33 (1H, t, J=7.6 Hz), 7.22 (1H, dd, J=7.6, 1.0 Hz), 7.13 (1H, t, J=53.5 Hz), 7.07 (1H, dd, J=7.8, 1.0 Hz), 6.95 (1H, t, J=54.8 Hz), 6.52 (1H, s), 3.91 (3H, s), 3.72 (3H, s), 2.92-2.83 (1H, m), 2.06 (1H, dd, J=12.7, 7.7 Hz), 1.57 (1H, dd, J=12.7, 7.5 Hz), 1.36 (3H, s), 1.24 (3H, d, J=6.8 Hz), 0.99 (3H, s).

A composition comprising the Present compound and one or more ingredient(s) selected from the group consisting of an insecticidal active ingredient, a miticidal active ingredient, a nematicidal active ingredient, a plant growth regulatory ingredient, a synergist, and another ingredient for controlling a plant disease (hereinafter collectively referred to as "Present ingredient") may be applied to a plant or soil to control pests such as harmful arthropods, harmful nematodes, and plant pathogens. Also, the Present compound and the Present ingredient may be applied separately to control pests.

Examples of the insecticidal active ingredient, the miticidal active ingredient, and the nematicidal active ingredient include those specified by IRAC (Insecticide Resistance Action Committee) and the others.

The plant growth regulatory ingredient indicates an ingredient for controlling plant growth such as promotion of fruit setting and promotion of rooting, and examples thereof include indolebutyric acid.

The synergist indicates an ingredient which potentiates the efficacy of another agent when used in admixture with said agent, and examples thereof include piperonyl butoxide.

Examples of the ingredient for controlling a plant disease include a fungicidal active ingredient. The fungicidal active ingredient is an ingredient for use in protecting a plant from diseases derived from plant pathogens (e.g., filamentous fungi or bacteria), and examples thereof include those specified by FRAC (Fungicide Resistance Action Committee) and the others.

Hereinafter, examples of the combination of the Present compound and the Present ingredient are described. For example, "tebuconazole+SX" indicates the combination of tebuconazole and SX. The abbreviation of "SX" indicates any one compound selected from the Present compound. Also, the number in parentheses represents the CAS registration number.

tebuconazole+SX, prothioconazole+SX, metconazole+SX, ipconazole+SX, triticonazole+SX, difenoconazole+SX, imazalil+SX, triadimenol+SX, tetraconazole+SX, flutriafol+SX, bromuconazole+SX, propiconazole+SX, mefentrifluconazole+SX, ipfentrifluconazole+SX, epoxiconazole+SX, cyproconazole+SX, mandestrobin+SX, azoxystrobin+SX, pyraclostrobin+SX, trifloxystrobin+SX, fluoxastrobin+SX, picoxystrobin+SX, fenamidone+SX, dimoxystrobin+SX, metominostrobin+SX, pyribencarb+SX, sedaxane+SX, penflufen+SX, fluxapyroxad+SX, fluopyram+SX, benzovindiflupyr+SX, boscalid+SX, carboxin+SX, penthiopyrad+SX, flutolanil+SX,bixafen+SX,pydiflumetofen+SX,
3-difluoromethyl-N-(7-fluoro-1,1,3-trimethylindan-4-yl)-1-methylpyrazole-4-carboxamide (1383809-87-7)+SX, N-cyclopropyl-3-(difluoromethyl)-5-fluoro-N-(5-chloro-2-iso propylbenzyl)-1-methyl-1H-pyrazole-4-carboxamide (1255734-28-1)+SX,
3-difluoromethyl-1-methyl-N-(1,1,3-trimethylindan-4-yl) pyrazole-4-carboxamide (141573-94-6)+SX, 3-difluoromethyl-1-methyl-N-[(3R)-1,1,3-trimethylindan-4-yl]pyrazole-4-carboxamide (1352994-67-2)+SX, metalaxyl+SX, metalaxyl-M+SX, metrafenone+SX, cyflufenamid+SX, proquinazid+SX,
3-chloro-5-phenyl-6-methyl-4-(2,6-difluorophenyl) pyridazine (1358061-55-8)+SX,
1-(2-{[1-(4-chlorophenyl)-1H-pyrazol-3-yl]oxymethyl}-3-meth ylphenyl)-4-methyl-1,4-dihydrotetrazol-5-one (1472649-01-6)+SX,
4-(2-bromo-4-fluorophenyl)-N-(2-chloro-6-fluorophenyl)-1,3-dimethyl-1H-pyrazol-5-amine (1362477-26-6)+SX, fenpicoxamid+SX,
N'-(2,5-dimethyl-4-phenoxyphenyl)-N-ethyl-N-methylmethanimidamide (1052688-31-9)+SX, isotianil+SX, oxolinic acid+SX, ferimzone+SX, phthalide+SX, kasugamycin+SX, tebufloquin+SX, quinofumelin+SX, fenpyrazamine+SX, procymidone+SX, fludioxonil+SX, tolclofos-methyl+SX, thiabendazole+SX, ethaboxam+SX, picarbutrazox+SX, oxathiapiprolin+SX, iminoctadine triacetate+SX, iminoctadine albesilate+SX, fenpropimorph+SX, fenpropidin+SX, spiroxamine+SX, chlorothalonil+SX, folpet+SX, captan+SX, thiram+SX, silthiofam+SX, mancozeb+SX, cartap+SX, clothianidin+SX, thiamethoxam+SX, imidacloprid+SX, thiacloprid+SX, flupyradifurone+SX, sulfoxaflor+SX, triflumezopyrim+SX, dicloromezotiaz+SX, beta-cyfluthrin+SX, tefluthrin+SX, fipronil+SX, chlorantraniliprole+SX, cyantraniliprole+SX, tetraniliprole+SX, thiodicarb+SX, carbofuran+SX, fluxametamide+SX, afoxolaner+SX, fluralaner+SX, broflanilide+SX, abamectin+SX, fluensulfone+SX, fluazaindolizine+SX, tioxazafen+SX, (E)-N-{1-[(6-chloropyridin-3-yl)methyl]pyridin-2(1H)-ylidene}-2,2,2-trifluoroacetamide (1689566-03-7)+SX, Mycorrhizal Fungi+SX, *Bacillus firmus*+SX, *Bacillus amyloliquefaciens*+SX, *Pasteuria nishizawae*+SX, *Pasteuria penetrans*+SX.

Examples of the ratio of the Present compound and the Present ingredient include, but are not limited to, 1000:1 to 1:1000, 500:1 to 1:500, 100:1 to 1:100, 50:1 to 1:50, 20:1 to 1:20, 10:1 to 1:10, 3:1 to 1:3, 1:1 to 1:500, 1:1 to 1:100, 1:1 to 1:50, 1:1 to 1:20, and 1:1 to 1:10 in the ratio by weight (Present Compound:Present ingredient).

Applying the Present compound to a plant achieves efficacies for promoting the plant growth such as the increase in the rate of seedling establishment, increase in the number of healthy leaves, increase in the height of the plant, increase in the weight of the plant, increase in the leaf area, increase in the number or weight of seeds or fruits, increase in the number of occasion of flower setting or fruit setting, and promotion in the growth of a root. Also, applying the Present compound to a plant achieves the improvement in tolerance to abiotic stresses such as temperature stresses (for example, high-temperature stress or low-temperature stress), water stresses (for example, drought stress or excess water stress), and salt stresses.

Next, Formulation Examples are shown below.

Formulation Example 1

Any one of the Present compound (50 parts), calcium lignin sulfonate (3 parts), magnesium lauryl sulfate (2 parts), and synthetic hydrated silicon oxide (45 parts) are fully ground and mixed to obtain each formulation.

Formulation Example 2

Any one of the Present compound (20 parts) and sorbitan trioleate (1.5 parts) are mixed with an aqueous solution (28.5 parts) comprising polyvinyl alcohol (2 parts), and the resulting mixture is finely ground by a wet grinding method. Then, an aqueous solution (40 parts) comprising xanthane gum (0.05 parts) and aluminum magnesium silicate (0.1 part) is added thereto, propylene glycol (10 parts) is further added thereto, and the resulting mixture is mixed with stirring to obtain each formulation.

Formulation Example 3

Any one of the Present compound (2 parts), kaolin clay (88 parts), and talc (10 parts) are fully ground and mixed to obtain each formulation.

Formulation Example 4

Any one of the Present compound (5 parts), polyoxyethylene styryl phenyl ether (14 parts), calcium dodecylbenzenesulfonate (6 parts), and xylene (75 parts) are fully mixed to obtain each formulation.

Formulation Example 5

Any one of the Present compound (2 parts), synthetic hydrated silicon oxide (1 part), calcium lignin sulfonate (2 parts), bentonite (30 parts), and kaolin clay (65 parts) are fully ground and mixed, and then water is added thereto, the resulting mixture is fully kneaded, and granulated and dried to obtain each formulation.

Formulation Example 6

A mixture of polyoxyethylene alkyl ether sulfate ammonium salt and white carbon (weight ratio 1:1) (35 parts), any one of the Present compound (20 parts), and water (45 parts) are fully mixed to obtain each formulation.

Test Example 1

A plastic pot was filled with soil, thereto wheat (cultivar. Shirogane) was seeded, and the wheat was grown in a greenhouse for nine days. Separately, the Present Compound (1), the Present Compound (2), or the Present Compound (3) formulated according to the process described in the Formulation Example 6 was mixed with water such that each concentration of the Present compound was 500 ppm. Said mixture was sprayed to the foliar parts so as to adhere adequately onto the surfaces of leaves of the above wheat. After spraying the mixture, the wheat was air-dried, cultivated at 20° C. under lighting for five days, and then spores of *Puccinia recondita* were inoculated by dusting thereto. After the inoculation, the wheat was placed at 23° C. under dark and humid condition for one day, then cultivated at 20° C. under lighting for eight days, and the lesion area was examined. From the test results, each lesion area in the group of wheat treated with the Present Compound (1), the Present Compound (2), or the Present Compound (3) was 10% or less as compared to the lesion area in the untreated group of wheat.

Test Example 2

A plastic pot was filled with soil, thereto barley (cultivar. *Nishinohoshi*) was seeded, and the barley was grown in a greenhouse for seven days. Separately, the Present Compound (2) or the Present Compound (3) formulated according to the process described in the Formulation Example 6 was mixed with water such that the concentration of the Present compound was 500 ppm. Said mixture was sprayed to the foliar parts so as to adhere adequately onto the surfaces of leaves of the above barley. After spraying the mixture, the barley was air-dried, and two days after the application, an aqueous suspension of spores of *Pyrenophora teres* was inoculated by spraying thereto. After the inoculation, the barley was placed at 23° C. in daytime and at 20° C. in nighttime in a greenhouse under humid condition for three days, then cultivated in a greenhouse for seven days, and then the lesion area was examined. From the test results, each lesion area in the group of barley treated with the Present Compound (2) or the Present Compound (3) was 10% or less as compared to the lesion area in the untreated group of barley.

INDUSTRIAL APPLICABILITY

The Present compound has control efficacies against plant diseases and is useful as an active ingredient of an agent for controlling plant diseases.

The invention claimed is:

1. An imide compound represented by formula (I)

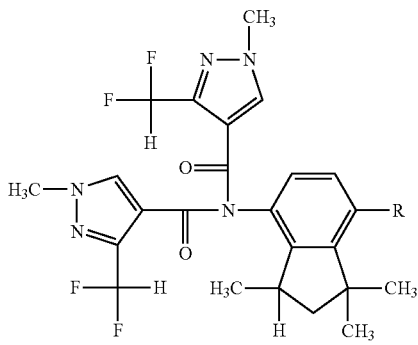

wherein R represents a fluorine atom or a hydrogen atom.

2. The imide compound according to claim 1, wherein the imide compound represented by formula (I) is an imide compound represented by formula (II)

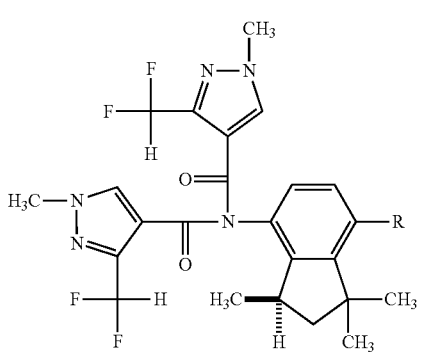

wherein R represents a fluorine atom or a hydrogen atom.

3. An agent for controlling a plant disease comprising the imide compound according to claim 1 and an inert carrier.

4. A method for controlling a plant disease which comprises applying an effective amount of the imide compound according to claim 1 to a plant or soil.

5. A method for controlling a plant disease which comprises applying an effective amount of the imide compound represented by formula (II) according to claim 2 to a plant or soil.

6. A composition comprising an imide compound represented by formula (I)

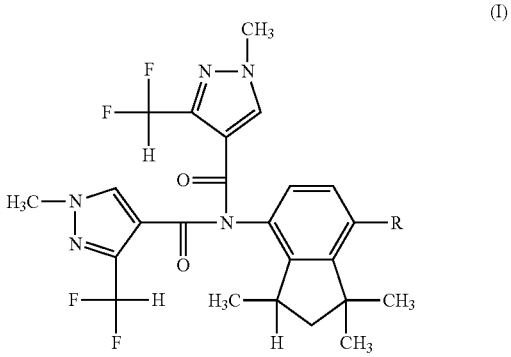

wherein R represents a fluorine atom or a hydrogen atom, and one or more ingredient(s) selected from the group consisting of an insecticidal active ingredient, a miticidal active ingredient, a nematicidal active ingredient, a plant growth regulatory ingredient, a synergist, and another ingredient for controlling a plant disease.

* * * * *